US012661241B2

(12) United States Patent
Siccardi et al.

(10) Patent No.: US 12,661,241 B2
(45) Date of Patent: Jun. 23, 2026

(54) DEVICE FOR SHAPING AND CUTTING A BONE GRAFT

(71) Applicant: MEDACTA INTERNATIONAL SA, Castel San Pietro (CH)

(72) Inventors: Francesco Siccardi, Castel San Pietro (CH); Massimiliano Bernardoni, Castel San Pietro (CH); Antonino Romeo, Castel San Pietro (CH); Andrea Rosa, Castel San Pietro (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 707 days.

(21) Appl. No.: 18/012,849

(22) PCT Filed: Jul. 8, 2021

(86) PCT No.: PCT/IB2021/056124
§ 371 (c)(1),
(2) Date: Dec. 23, 2022

(87) PCT Pub. No.: WO2022/013686
PCT Pub. Date: Jan. 20, 2022

(65) Prior Publication Data
US 2023/0270565 A1 Aug. 31, 2023

(30) Foreign Application Priority Data
Jul. 13, 2020 (IT) ........................ 102020000016882

(51) Int. Cl.
A61B 17/32 (2006.01)
A61F 2/28 (2006.01)
A61F 2/46 (2006.01)

(52) U.S. Cl.
CPC .... *A61F 2/4644* (2013.01); *A61F 2002/2835* (2013.01); *A61F 2002/4645* (2013.01);
(Continued)

(58) Field of Classification Search
None
See application file for complete search history.

(56) References Cited

U.S. PATENT DOCUMENTS 7,802,503 B2 * 9/2010 Couvillion ............... B26D 1/08
83/762
7,955,336 B2 * 6/2011 Gil ........................ A61F 2/4644
606/79

(Continued)

FOREIGN PATENT DOCUMENTS

EP 3222253 A1 * 9/2017 ........... A61F 2/4081

OTHER PUBLICATIONS

International Search Report and Written Opinion issued in PCT/IB2021/056124, mailed Oct. 14, 2021, 13 pages.

*Primary Examiner* — Ann Hu
(74) *Attorney, Agent, or Firm* — Meunier Carlin & Curfman LLC

(57) ABSTRACT
A device for shaping and cutting a bone graft comprises a main body extending along a longitudinal axis from a lower end to an upper end and having inside it a housing for the insertion of the bone graft to be shaped, an upper opening located at the upper end for the insertion of the bone graft into the housing, a lower support designed to support the bone graft, and an upper surface defining a cutting plane placed at the upper end and containing said upper opening, wherein the cutting plane is inclined with respect to the longitudinal axis by an angle ranging between 90° and 30°, preferably between 90° and 60°.

14 Claims, 12 Drawing Sheets

(52) U.S. Cl.
CPC ................. *A61F 2002/4649* (2013.01); *A61F*
*2310/00359* (2013.01)

(56)                    References Cited

U.S. PATENT DOCUMENTS

|              |       |         |           |              |
|--------------|-------|---------|-----------|--------------|
| 9,700,438    | B2 *  | 7/2017  | Kehres    | B25B 5/163   |
| 9,918,769    | B2 *  | 3/2018  | Provencher | A61F 2/4644 |
| 11,185,417   | B2 *  | 11/2021 | Boileau   | A61B 17/1637 |
| 11,213,406   | B2 *  | 1/2022  | Rodriguez | A61F 2/4644  |
| 12,102,546   | B2 *  | 10/2024 | Settke    | A61F 2/4644  |
| 12,478,384   | B2 *  | 11/2025 | Evans     | A61F 2/30756 |
| 2007/0118050 | A1 *  | 5/2007  | Accordino | A61B 10/025  |
|              |       |         |           | 600/567      |
| 2007/0173852 | A1 *  | 7/2007  | Gil       | A61F 2/4644  |
|              |       |         |           | 606/87       |
| 2008/0255562 | A1    | 10/2008 | Gil et al. |             |
| 2012/0253350 | A1 *  | 10/2012 | Anthony   | A61B 17/14   |
|              |       |         |           | 606/87       |
| 2013/0325020 | A1 *  | 12/2013 | Yoko      | A61B 17/1764 |
|              |       |         |           | 606/88       |
| 2014/0276846 | A1 *  | 9/2014  | Mauldin   | A61B 17/1664 |
|              |       |         |           | 606/80       |
| 2015/0297361 | A1 *  | 10/2015 | Kehres    | B25B 5/102   |
|              |       |         |           | 83/13        |
| 2019/0358045 | A1    | 11/2019 | Boileau et al. |         |

* cited by examiner

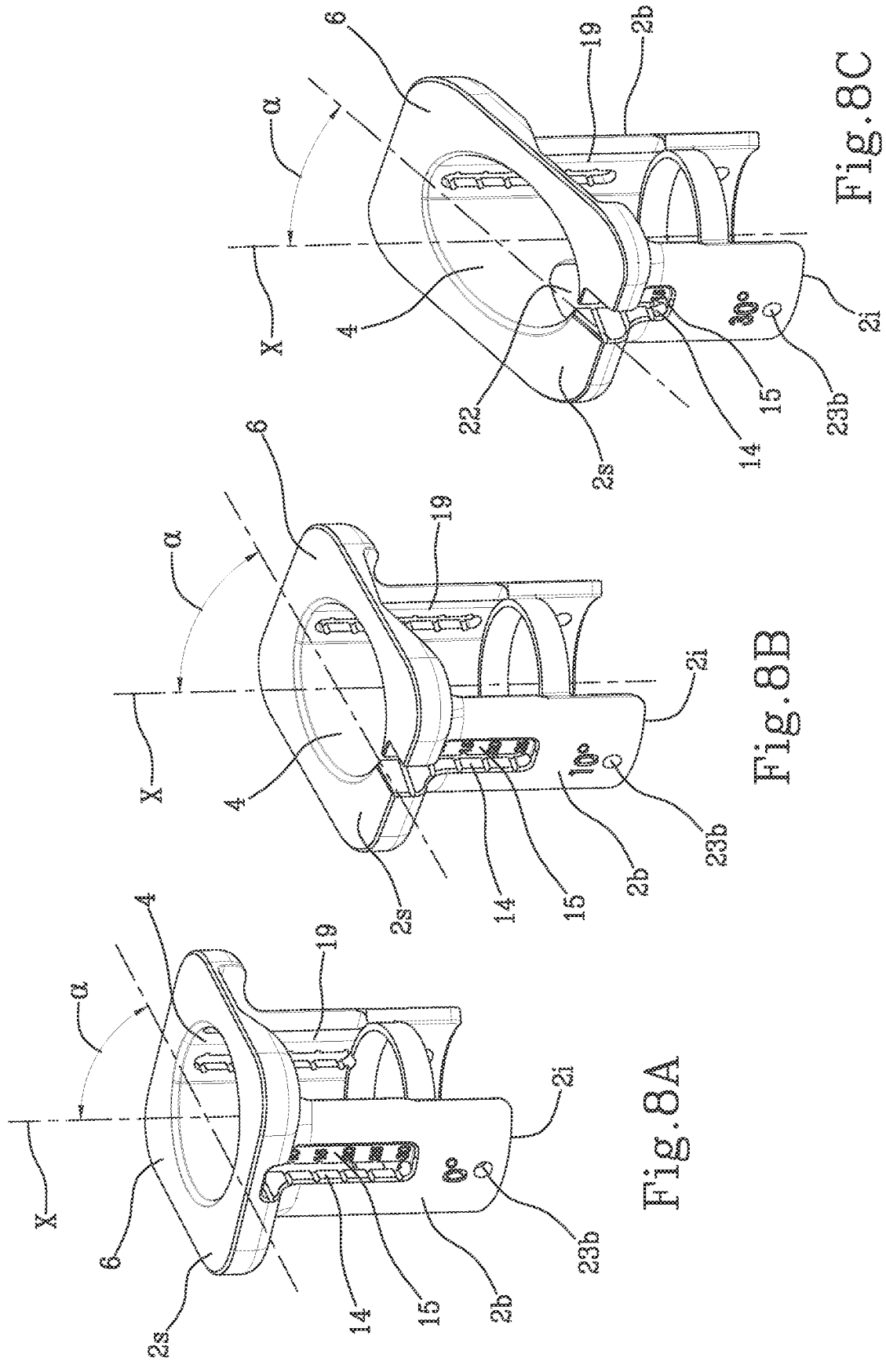

DEVICE FOR SHAPING AND CUTTING A BONE GRAFT

FIELD OF APPLICATION

The present invention relates to a device for shaping and cutting a bone graft.

In the case of lateralisation of the shoulder, or bone deformations caused by degenerative diseases of the glenoid, there is a need to find a bone graft that is able to move the joint plane in a lateral direction, in order to restore the correct function of the joint.

PRIOR ART

Currently, a bone graft interposed between the bone structure of the glenoid and the part of the implant that lies on the same glenoid is used in order to lateralise the shoulder joint. This bone graft, positioned in this way, moves the joint plane in a lateral direction in order to restore the natural functionality of the joint.

In the prior art, the autogenous bone graft is extracted from the patient's own bone structure. In fact, during the operations of shoulder joint reconstruction, the humeral head is removed and replaced with a prosthetic humeral head. The glenoid is also replaced by inserting a suitable prosthesis. By exploiting the removal of the humeral head, therefore, the surgeon can extract from it the bone graft necessary for the lateralisation of the joint. To do this, in the prior art, the surgeon proceeds with the insertion of a guide wire, called Kirchner wire, in the correct position on the humeral head. By means of said wire, a cutter having a cylindrical shape is brought into contact with the humeral head, by means of which a cylinder portion of bone can be carved in the humeral head. To extract said portion of carved bone, the portion of bone containing the carved portion is then cut along an appropriate plane. Said cut is made freehand by the surgeon. At this point the bone graft can be extracted; the bone graft that is extracted may already have the geometry established in the pre-operative phase (in terms of height and inclination of the base surfaces) or it may need further processing in order to meet the requirements that are necessary for the correct lateralisation of the joint. In fact, it is often necessary for the bone graft to have regular cutting surfaces and for its base faces to have mutually predefined inclinations. Therefore, depending on the type of surgery and the bone conformation of the individual patient, it may be necessary to have a bone graft with base faces that are parallel to each other, respectively, inclined to each other by a predefined angle in order to restore the proper joint function.

If the bone graft is shaped in situ in the humeral head, there may be dimensional and/or geometric errors in the preparation of the bone graft and/or of the glenoid such that they do not meet the dimensional and geometric requirements that are necessary for the proper lateralisation of the joint. In such a circumstance, it is not possible to achieve the desired final result that had been planned in the pre-operative phase.

Therefore, it is often preferable to extract a cylindrical bone graft and shape it at a later stage after extraction.

Once the bone graft has been extracted, therefore, it is necessary to prepare the graft so that it respects the parameters established in the pre-operative phase.

In the technique currently in use, this processing is done on a service table that is present in the operating room, known as a back table, where the surgeon or an assistant of him shapes what has been extracted from the patient. More specifically, the surgeon checks that the bone graft is correctly sized (i.e. that the axial development thereof is sufficient) and checks that the basic faces of the bone graft have the predefined inclinations. If one of these parameters does not comply with what had been planned in the pre-operative phase, the surgeon proceeds with shaping the bone graft in order to bring the parameters listed above back in accordance with what had been planned. These bone graft rearrangement operations are currently carried out freehand by the surgeon, with many drawbacks.

In fact, a cutting error in the rearrangement phase can lead to obtaining a bone graft that is too small (i.e. with insufficient axial development) for the required lateralisation, compromising the success of the operation. Similarly, an incorrect correction of the inclination of one (or both) of the bases of the bone graft can lead, also in this case, to an unsuccessful operation. Unfortunately, as these operations are carried out freehand by the surgeon, it is not uncommon to assume approximate corrections to the shape of the bone graft, which can lead to poor efficiency of the prosthesized joint.

In addition, if the error made by the surgeon at this stage is particularly significant, the bone graft may no longer be usable, which would jeopardise the success of the surgery and the impossibility of using an autogenous bone graft.

In addition, the handling of the bone graft during the steps of freehand shaping thereof by the surgeon is difficult due to the presence of body fluids on the graft, the limited sizes thereof and the possible poor quality of the bone from which it was extracted.

Last but not least, it is a perceived drawback of the state of the art that the step of shaping the bone graft has to be done during the shoulder surgery phases, with a consequent increase in the patient's operating times and costs for the hospital.

An object of the present invention is to overcome the drawbacks of the prior art.

In particular, it is an object of the present invention to propose a device for shaping and cutting a bone graft which avoids performing the shaping and cutting completely freehand, but which provides the aid of specifically designed instrumentation which facilitates this operation for the surgeon. Therefore, it is an object of the present invention to provide a device for shaping and cutting a bone graft which allows shaping a bone graft having the correct height and regular opposite base surfaces and having a predefined and correct inclination. Therefore, the object of the present invention is to realise a device for shaping and cutting a bone graft which offers a wide range of dimensional selection with regard to both the height of the graft and the angle of the upper surface.

A further object of the present invention is to realise a device for shaping and cutting a bone graft which allows an easy handling for the surgeon even in the presence of limited sizes or of body fluids and which gives the possibility of shaping on the back table.

It is also an object of the present invention to provide a device for shaping and cutting a bone graft that reduces the operating times and allows the graft to be made even in case of poor bone quality.

These and further purposes and advantages are achieved by a device for shaping and cutting a bone graft device according to the appended claims.

Abstract

A first aspect of the present invention provides for a device for shaping and cutting a bone graft comprising a main body extending along a longitudinal axis, from a lower end to an upper end, and having inside it a housing for the insertion of the bone graft to be shaped. The main body comprises an upper opening, located at the upper end, for the insertion of the bone graft into the housing, and a lower support designed to support the bone graft. The main body comprises an upper surface defining a cutting plane, placed at the upper end and containing the upper opening. The main body is interchangeable in such a manner that the upper surface is inclined with respect to the longitudinal axis by an angle ranging between 90° and 30°, preferably between 90° and 60°, depending on the main body selected and associated with the lower support.

The device for shaping and cutting a bone graft further comprises an engagement and adjustment body, which can be coupled to the main body, having an engagement portion, designed to receive in shape coupling the lower end of the main body, and a base portion, defining the lower support, mobile along the longitudinal axis.

The base portion comprises a flange head, designed to receive in support the bone graft, connected to a threaded shank that can be screwed inside a threaded hole present in the engagement and adjustment portion, and a gripping and handling element, connected to the threaded shank in a position opposite to the flange head, to rotate the support portion and cause it to shift vertically to adjust the position of the flange head inside the housing of the main body.

The flange head of the base portion of the engagement and adjustment body comprises a central cavity, coaxial to the longitudinal axis, to receive in abutment a drilling tool used for the central bore of the bone graft.

The engagement and adjustment body comprises at least a first arm designed to guide the coupling between the main body and the engagement and adjustment body and to permanently lock the bone graft within the main body during the cutting step, by imparting a force orthogonal to the longitudinal axis on the bone graft.

The engagement and adjustment body comprises at least a second arm designed to guide the coupling between the main body and the engagement and adjustment body.

The main body comprises at least one window, located on a side wall delimiting the housing of the bone graft, designed for the insertion of the first arm of the engagement and adjustment body.

The main body comprises at least one groove, located on a side wall delimiting the housing of the bone graft, designed to house the second arm of the engagement and adjustment body.

The device comprises a locking pin of the first arm, to lock the latter in a clamping configuration wherein the first arm holds the bone graft in a predefined locked position to proceed with the cutting and prevent its shifting along the longitudinal axis.

The device also comprises a centring and locking mechanism for the correct coupling and locking between the main body and the engagement and adjustment body.

The centring and locking mechanism comprises a ball push-button, located on the engagement and adjustment body, which can be engaged inside a hole realized in the main body.

The main body comprises at least one slit, on a side wall delimiting the housing of the bone graft, having a respective graduated scale, designed to indicate the cutting height of the bone graft.

The main body also comprises a second slit, opposite the first slit on the side wall delimiting the housing of the bone graft, having a respective graduated scale, designed to indicate the cutting height of the bone graft.

In a second aspect, the invention provides for a kit for shaping and cutting a bone graft comprising a device for shaping and cutting a bone graft device in accordance with the foregoing and a plurality of main bodies each having an upper surface defining a cutting plane, each having an inclination that is different from each other. Each main body of the plurality of main bodies included in the kit has a respective upper surface having an inclination that is different from the others, predetermined with respect to the longitudinal axis by an angle ranging between 90° and 30°, preferably between 90° and 60°.

BRIEF DESCRIPTION OF THE DRAWINGS

The present invention will be made clearer by the following detailed description, with reference to the accompanying drawings provided by way of example only, wherein:

FIGS. 8A, 8B and 8C show three alternative configurations of a component of the device subject matter of the present invention;

DETAILED DESCRIPTION

In the above figures, a device for shaping and cutting a bone graft in accordance with the present invention has been collectively referred to as 1.

The device 1, described below, is used to cut and shape a bone graft 100 obtained from the head of the humerus, by using a surgical tool and applying a technique described hereinbelow.

The tool used to extract a bone graft is illustrated according to two different configurations, each used for a respective extraction method, in FIGS. 9A-9F and 10A-10C.

Figures 9A, 9B, 9C:
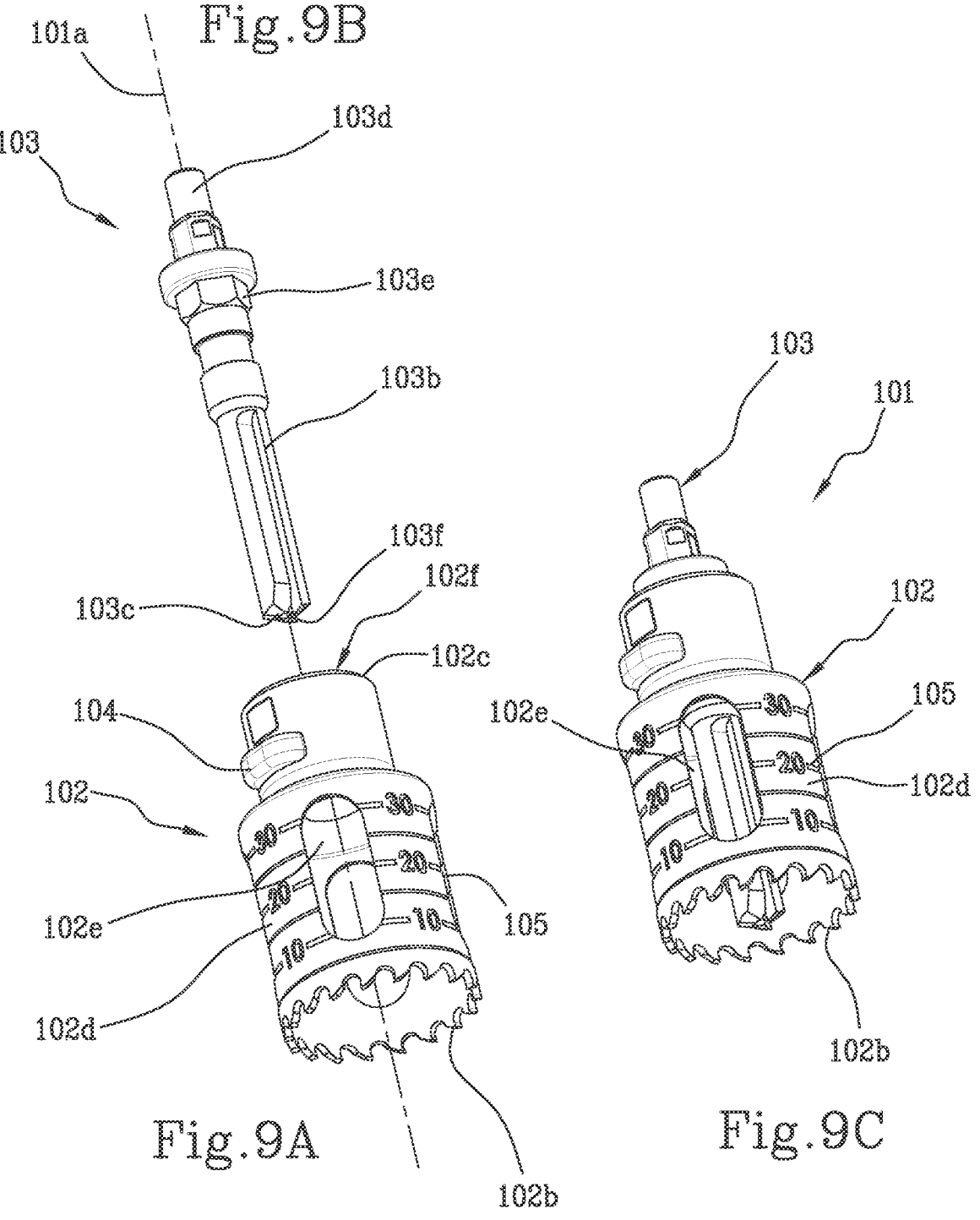
FIG. 9A shows a trephine, used to extract a bone graft from the head of the humerus.
FIG. 9B illustrates a cylindrical reamer to be used in conjunction with the trephine in FIG. 9A to core the bone graft.
FIG. 9C illustrates the cylindrical reamer of FIG. 9A coupled to the trephine of FIG. 9B.
Figure 9E:
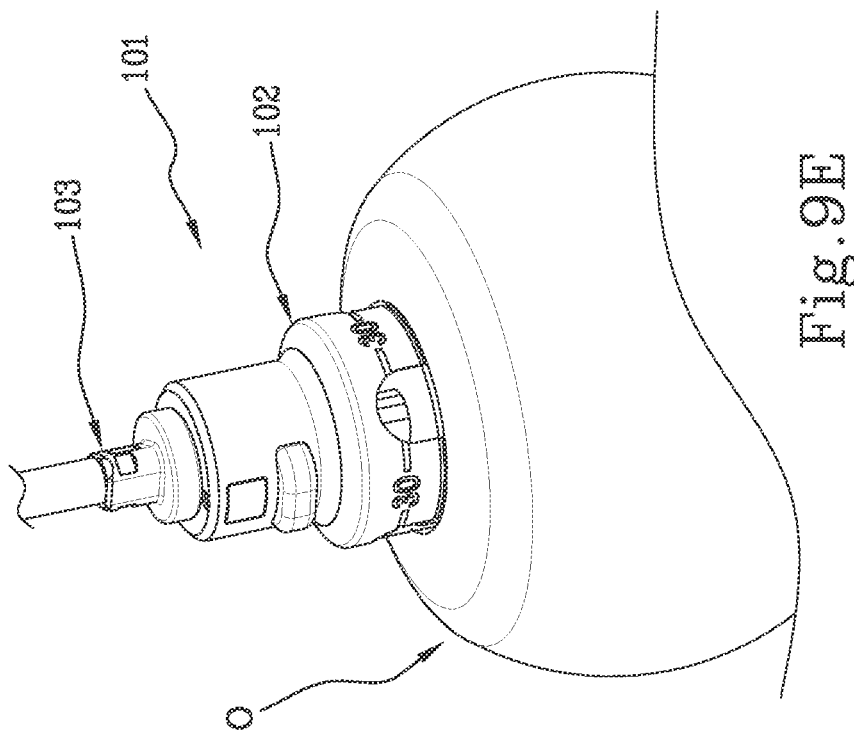
FIGS. 9D, 9E and 9F illustrate three steps for the extraction of the bone graft: paired hole and cylindrical reamers approaching the head of the humerus, insertion of the cutters into the bone, extraction of the cylindrical internally drilled graft.
Figure 9D:
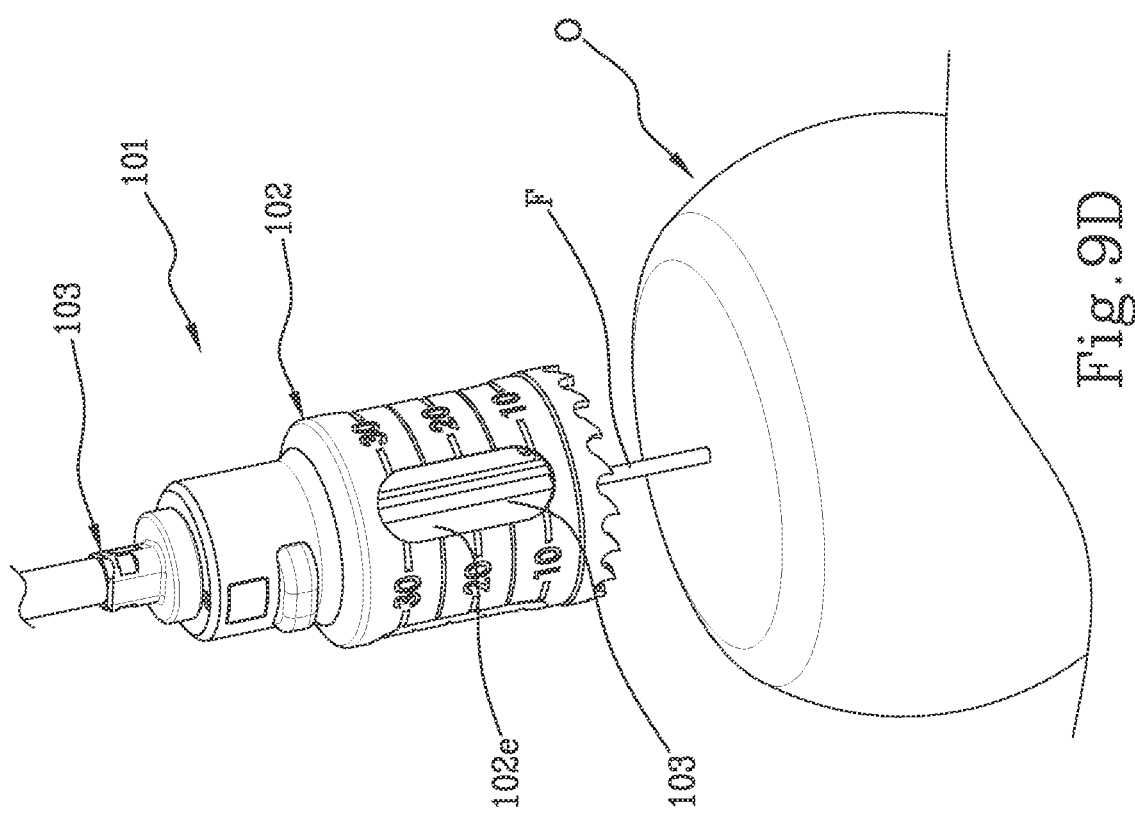
Figure 9F:
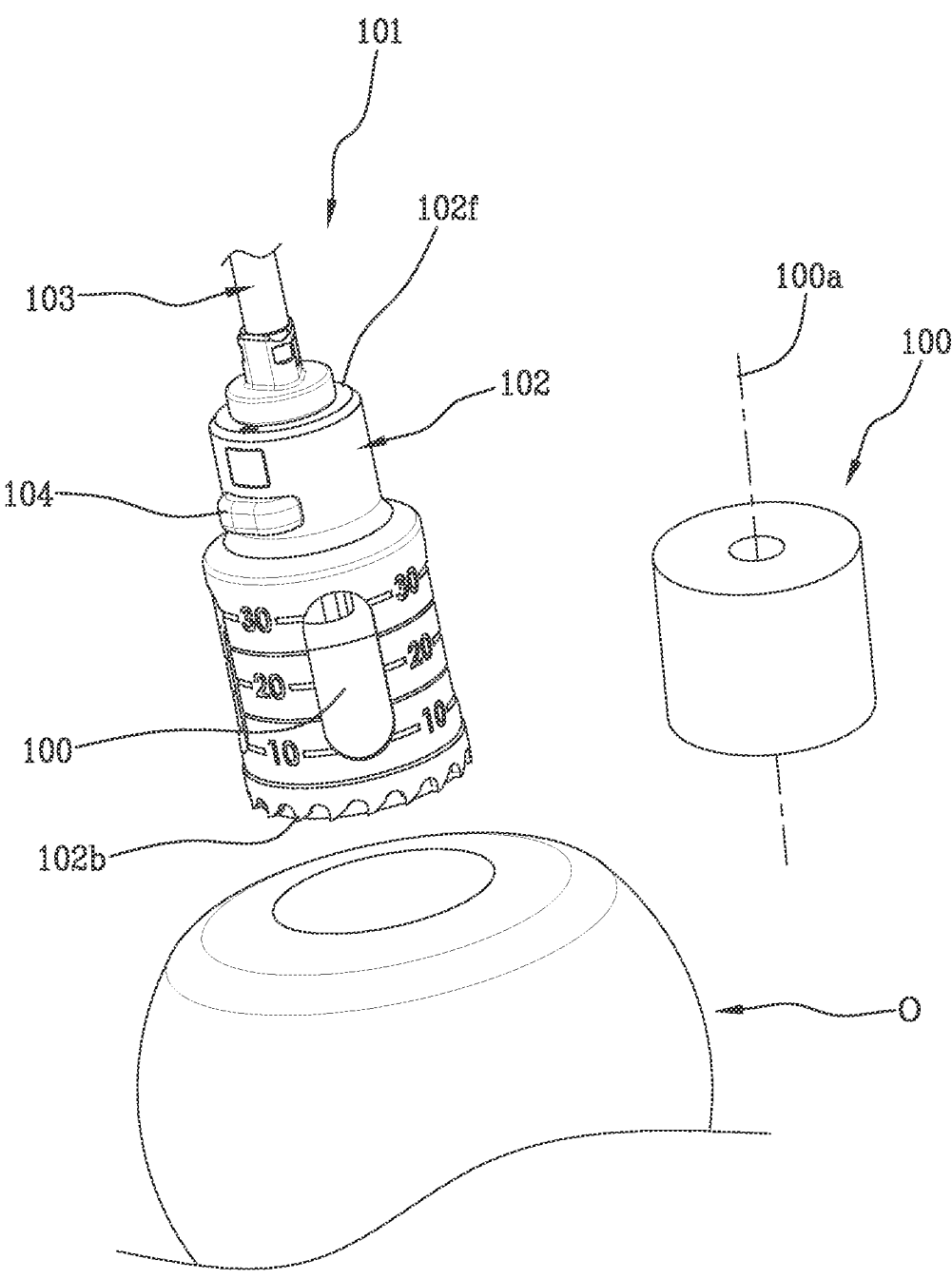

The bone graft 100 is taken from the humeral head O by means of a coring tool 101, 101' (illustrated in FIGS. 9C and 10A respectively) which consists of a trephine 102 (FIG. 9A) and a cylindrical reamer 103 (FIG. 9B). The first component 102, i.e. the trephine visible in FIG. 9A, is defined by a cylindrical body having a cylindrical side wall 102*d*, which is advantageously externally graduated, and by a circular cutting edge 102*b*, placed at a first end and delimiting the cylindrical side wall. The trephine 102 is used to cut the outer surface of the bone graft 100.

The trephine 102 further comprises a second end 102*c*, opposite to the cutting end, which acts as a connection with the cylindrical reamer 103, by means of a button 104 which allows the tool to be held in position.

The trephine 102 is internally hollow and has, at the second end 102*c*, an opening 102*f* through which the cylindrical reamer 103 is axially inserted. There is a graduated scale 105 on the outer surface of the cylindrical side wall 102*d* of the trephine 102, which serves to allow the surgeon to select the coring depth.

On the cylindrical side wall 102*d*, the trephine 102 has at least one, preferably two, windows 102*e* designed to allow the surgeon to see the coring depth having the graduated scale 105 as an external reference.

The tool can be available in different diameters and lengths depending on the size of the bone graft.

As mentioned above, the second component of the coring tool 101 is a cylindrical reamer 103 (FIG. 9B) having a longitudinally elongated shape along a developmental axis 101*a*, and cutting profiles that are present both along the side edges 103*b* developing longitudinally along the axis 101*a*, and at a free end thereof 103*c*.

The cylindrical reamer 103 comprises, at one end 103*d*, a portion for coupling a tool that rotates the cylindrical reamer 103.

The latter also has an interference portion 103*e* designed to couple with the trephine 102, to which it transmits rotation.

The cylindrical reamer 103 is inserted inside the trephine 102, as shown in FIGS. 9A-9C, through a hole 102*f* of the trephine placed at the end 102*c* opposite the cutting end, thus making it possible to obtain a coring tool 101 having cylindrical side walls provided with a cutting attachment edge 103*c* and a central axial blade 103*b*, in order to thus make a hollow cylindrical bone graft 100, provided with a central hole passing through the entire height of the graft, along the entire axis 100*a*. The cylindrical reamer 103, therefore, defines the inner diameter of the graft 100.

The cylindrical reamer 103 is assembled to the trephine 102 and, by means of the interference portion 103*e* (specifically countershaped to the central hole present in the trephine 102) of the mentioned cylindrical reamer 103, the torque that will be used to cut the bone is transferred to the trephine 102.

The cylindrical reamer 103 has an axial through-hole 103*f* to allow the tool to be inserted on the guide wire F (k-wire) and thus to guide the coring tool 101 during the preparation of the graft.

The cylindrical reamer 103 can be available in different diameters and lengths.

The coring tool can also be used in cases of poor bone quality or where the bone has an uneven surface.

Figure 10B:
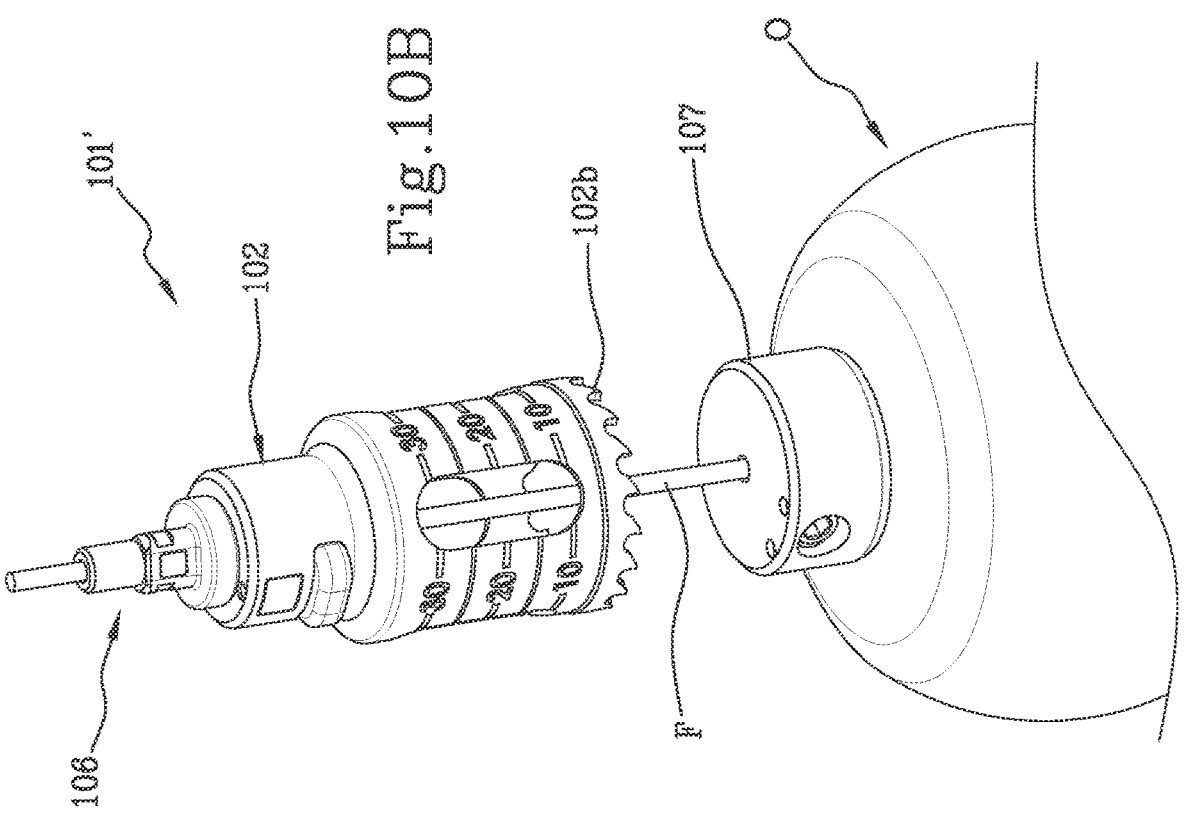
FIG. 10B illustrates the trephine assembled with the adapter of FIG. 10A, in a first step of use of coupling with a stabilising body that is fixed on the bone in order to guide the cutter during its use, in case of poor quality bone.
Figure 10A:
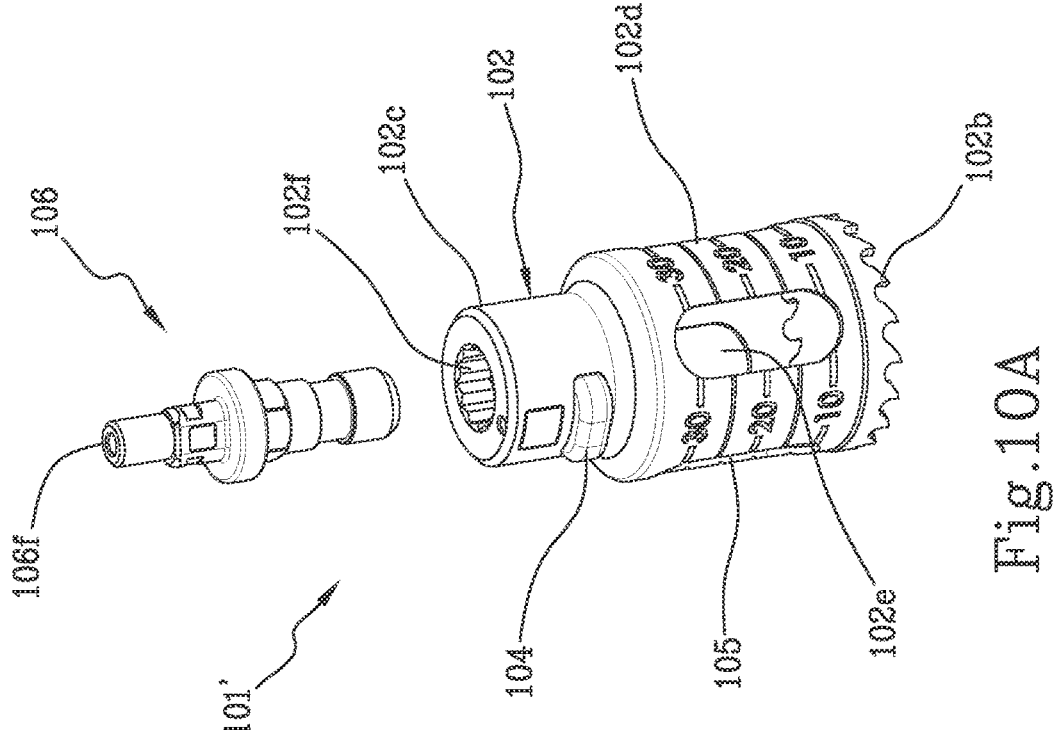
FIG. 10A shows an exploded view of the trephine of FIG. 9A and an adapter that guides the trephine on the guide wire (K-wire) and which transfers the torque to the cutter to cut the bone.
Figure 10C:
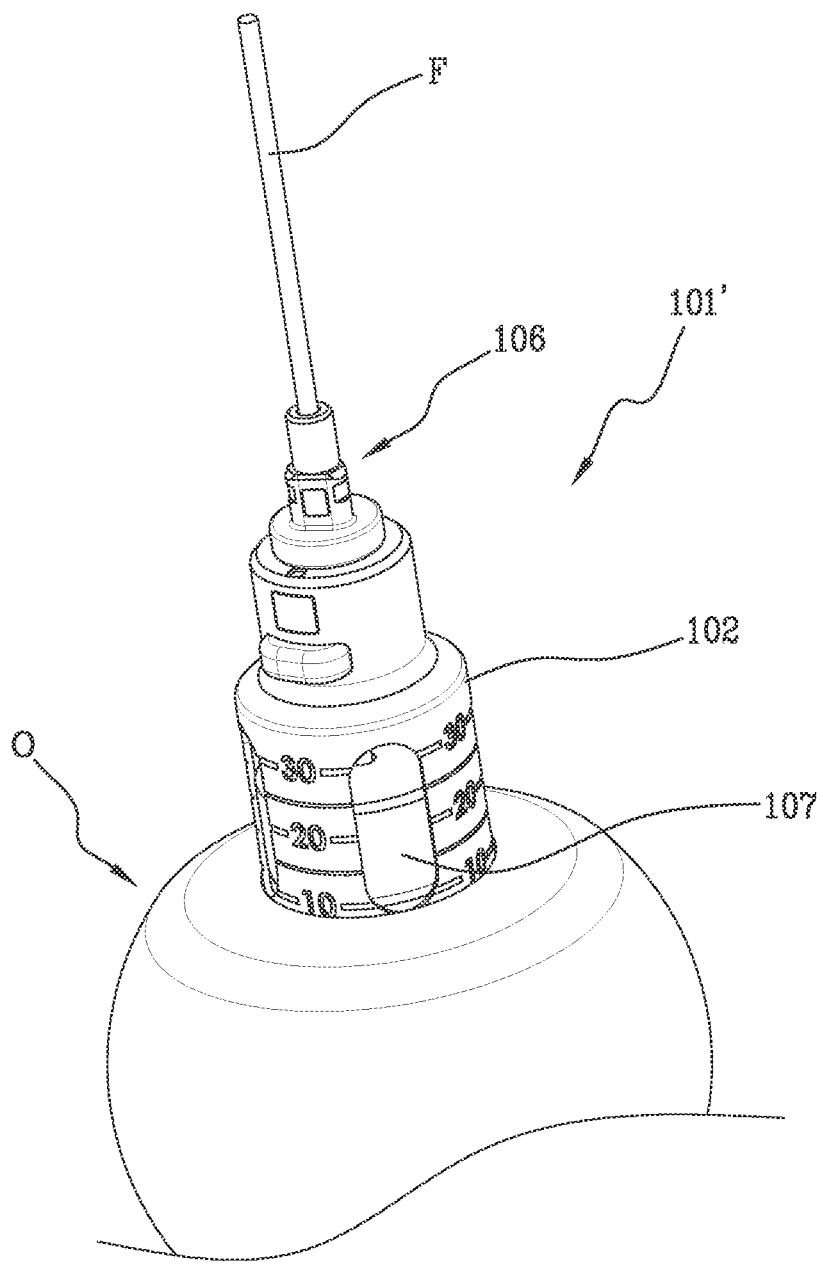
FIG. 10C shows a second step of use during which the cutter is digging into the bone to extract the graft.

A coring tool 101' used in case of poor bone quality is shown in FIGS. 10A-10C.

In such cases, the central cylindrical reamer is replaced by another component, which acts as an adapter 106, to guide the trephine 102 on the guide wire F (k-wire). The adapter has an elongated cylindrical shape with a hole 106*f* passing axially through the entire longitudinal extension of the adapter. The guide wire F passes through the hole 106*f* of the adapter 106.

The adapter 106 has a lower height than the cylindrical reamer 103, since it does not have to extend along the entire height of the trephine 102, as it does not have to drill centrally into the graft, but it only has to transfer the rotational torque to the trephine 102.

For this purpose, the adapter 106 comprises, like the cylindrical reamer 103, an interference portion 106*e* designed to couple with the trephine 102, to which it transmits the rotation.

The trephine 102 is identical to the one described above, and therefore it has a suitably shaped hole 102*f*, designed to couple to the interference portion 106*e*, into which the adapter 106 and, in particular, the interference portion 106*e* is inserted.

The coupling between the adapter 106 and the trephine 102 is similar to the one already described with reference to the coupling between the cylindrical reamer and the trephine, so as to transfer the torque that allows the trephine to cut the bone.

The trephine 102 is assembled to the adapter 106 which is inserted at the hole 102*f* located at the second end 102*c* of the trephine 102 and, by means of the interference portion 103*e* (specifically countershaped to the central hole present in the trephine 102), the torque that will be used to cut the bone is transferred to the trephine 102.

In order for the trephine to core the bone graft correctly, even in case of poor quality bone, a stabilising body 107 (FIG. 10B) is fixed on the bone by means of a guide wire F, to guide the cutter during its use. The dimensions of the stabilising body 107 are available in different diameters and lengths in order to match the dimension of the bone graft to be extracted.

Once the bone graft has been obtained, it has to be shaped: in particular, the height has to be adjusted and at least one of the two bases has to be cut according to a plane with an inclination designed to couple with the prosthesis, and the correct joint function restored.

The device 1, which is the subject matter of the present invention, is used for this shaping and cutting operation and is described in detail below.

The shaping and cutting device 1, illustrated in FIGS. 1-8C, serves to hold and keep stable the bone graft extracted according to the method and with the tool 101, 101' described above. It comprises a main body 2, having inside it a housing 3 for the insertion of the bone graft to be shaped.

The main body 2 extends along a longitudinal axis X, from a lower end 2*i* to an upper end 2*s*. It has an upper opening 4, located at the upper end 2*s*, through which the bone graft is inserted into the housing 3.

The device 1 further has a lower support 5 designed to support the bone graft.

At the upper end 2*s*, the central body 2 has an upper surface 6, defining a cutting plane, containing the upper opening 4; the upper surface 6 may be inclined with respect to the longitudinal axis X by an angle α ranging between 90° and 30°, preferably between 90° and 60°.

The main body 2 is interchangeable: different sizes in diameter and height of the main body 2 are provided. Depending on the desired inclination of the graft, a central body 2 is selected, to be associated with the lower support 5, having the upper surface 6 with a suitable inclination. The inclination of the upper surface 6 with respect to the longitudinal axis X forms an angle α ranging between 90° and 30°, preferably between 90° and 60°.

The central body 2 is therefore available with different angles of the upper surface 6, as shown in FIGS. 8A-8C where, by way of example only, main bodies 2 having surfaces inclined by 0°, 10° and 30° with respect to a plane orthogonal to the longitudinal axis X have been represented.

The interchangeability of the main body 2 allows the selection of the upper surface 6 with a desired inclination and appropriate to the geometry to be given to the bone graft 100.

Once the bone graft 100 is inserted and fixed inside the housing, the blade L (FIG. 2), by sliding on the cutting plane defined by the upper surface 6, cuts with precision the upper portion of the bone graft according to the inclination established in the pre-operative phase, considerably speeding up the shaping operation and guaranteeing a high precision in the cut and the correct desired inclination.

The device 1 further comprises an engagement and adjustment body 7, which can be coupled inferiorly to the main body 2.

Once the main body 2 has been selected and has the dimensions suitable for the bone graft to be obtained, it is coupled with the engagement and adjustment body 7.

The engagement and adjustment body 7 has an engagement portion 8, designed to receive in shape coupling the lower end 2i of the main body 2, and a base portion 9, defining the mentioned lower support 5 of the device 1. The base portion 9 is mobile along the longitudinal axis X so as to define the cutting height, and therefore the final height, of the bone graft.

The base portion 9 comprises a flange head 10, on which the bone graft rests, connected in the lower part thereof to a threaded shank 11 that can be screwed inside a threaded hole 12 present in the engagement portion 8, and a gripping and handling element 13, such as a knob, connected to the threaded shank 11 in a position opposite to the flange head 10. By means of the gripping and handling element 13, the threaded shank 11, and thus the flange head 10, are rotated and shifted upwards or downwards, thanks to the threaded coupling between the shank 11 and the hole 12, until the flange head 10, which defines the actual support plane of the bone graft, reaches the desired height within the housing 3 of the main body 2.

In detail, the main body 2 comprises, on a side wall 2b delimiting the housing of the bone graft 3, at least one slit 14 extended vertically, thus parallel to the longitudinal axis X, which gives visibility inside the housing 3 in order to be able to have visibility and precisely adjust the position of the flange head 10 in height. For a greater precision, the slit 14 is flanked by a respective graduated scale 15 designed to indicate the exact vertical position of the flange head 10 and thus the correct measurement of the height of the bone graft. This dimension is usually determined preoperatively, but the device subject matter of the present invention allows the geometry (in terms of height of the bone graft and inclination of the base surfaces) to be adjusted during the surgery shaping step. In fact, it is preferable to extract a bone graft with the maximum possible axial development, in order to shape the most appropriate height during surgery.

Advantageously, there is a similar second slit 16, opposite the first slit 14. The second slit 16 is also made on the side wall 2b delimiting the housing 3 of the bone graft, and has a respective graduated scale 17, designed to indicate the exact vertical position of the flange head 10 and, therefore, the correct measurement of the height of the bone graft. This second slit 16 allows for a better use of the device as it allows a control over the cutting height of the bone graft from the opposite side as well.

The engagement and adjustment body 7 comprises at least a first arm 18, projecting upwards from the engagement portion 8, in order to be coupled with the main body 2.

Said first arm 18 is designed to guide the coupling between the main body 2 and the engagement and adjustment body 7 itself, and mainly to permanently lock the bone graft within the main body 2 during the cutting step. The first arm 18, in fact, acts laterally on the bone graft imparting a force orthogonal to the longitudinal axis X thereon.

The main body 2 therefore comprises at least one window 19, on the side wall 2b delimiting the housing of the bone graft 3, designed for the insertion of the first arm 18 of the engagement and adjustment body 7, which allows a direct contact between the first arm 18 and the bone graft 100.

Figure 1:
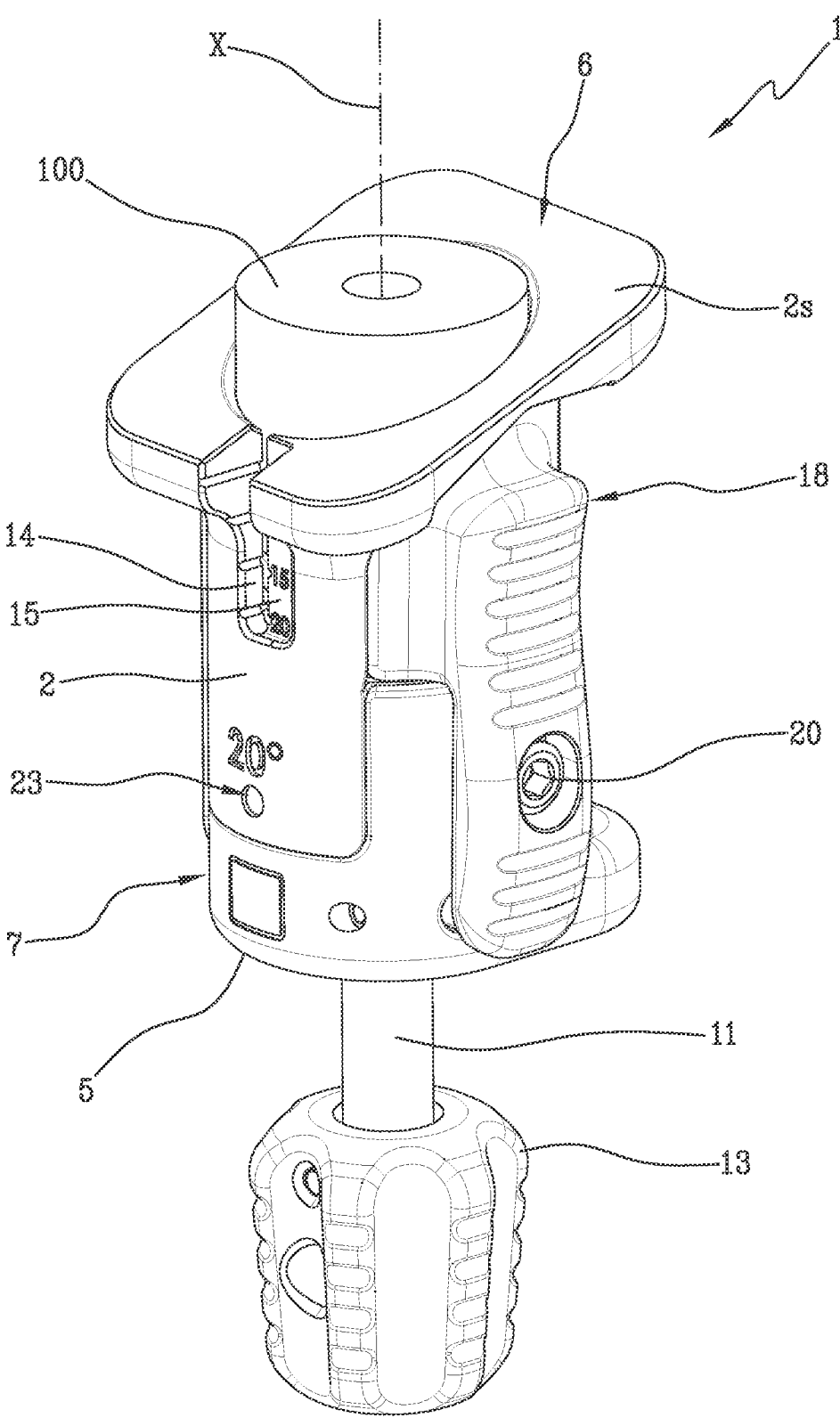
FIG. 1 illustrates a front perspective view of a device for shaping and cutting a bone graft in accordance with the present invention, associated with a bone graft yet to be shaped.
Figure 2:
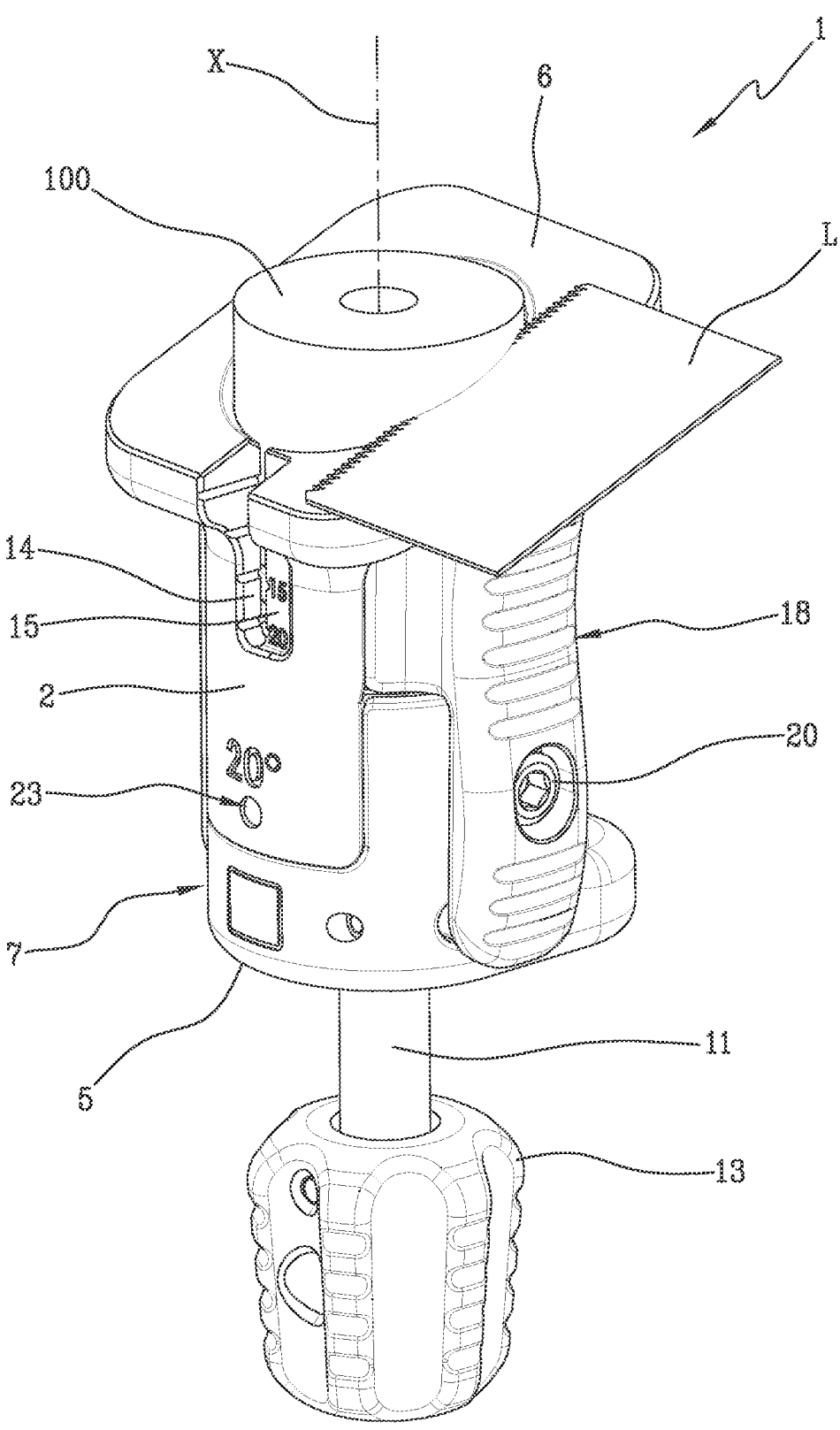
FIG. 2 illustrates a front perspective view of the device for shaping and cutting a bone graft illustrated in FIG. 1, associated with a bone graft and in the step of cutting and shaping the upper surface.
Figure 3:
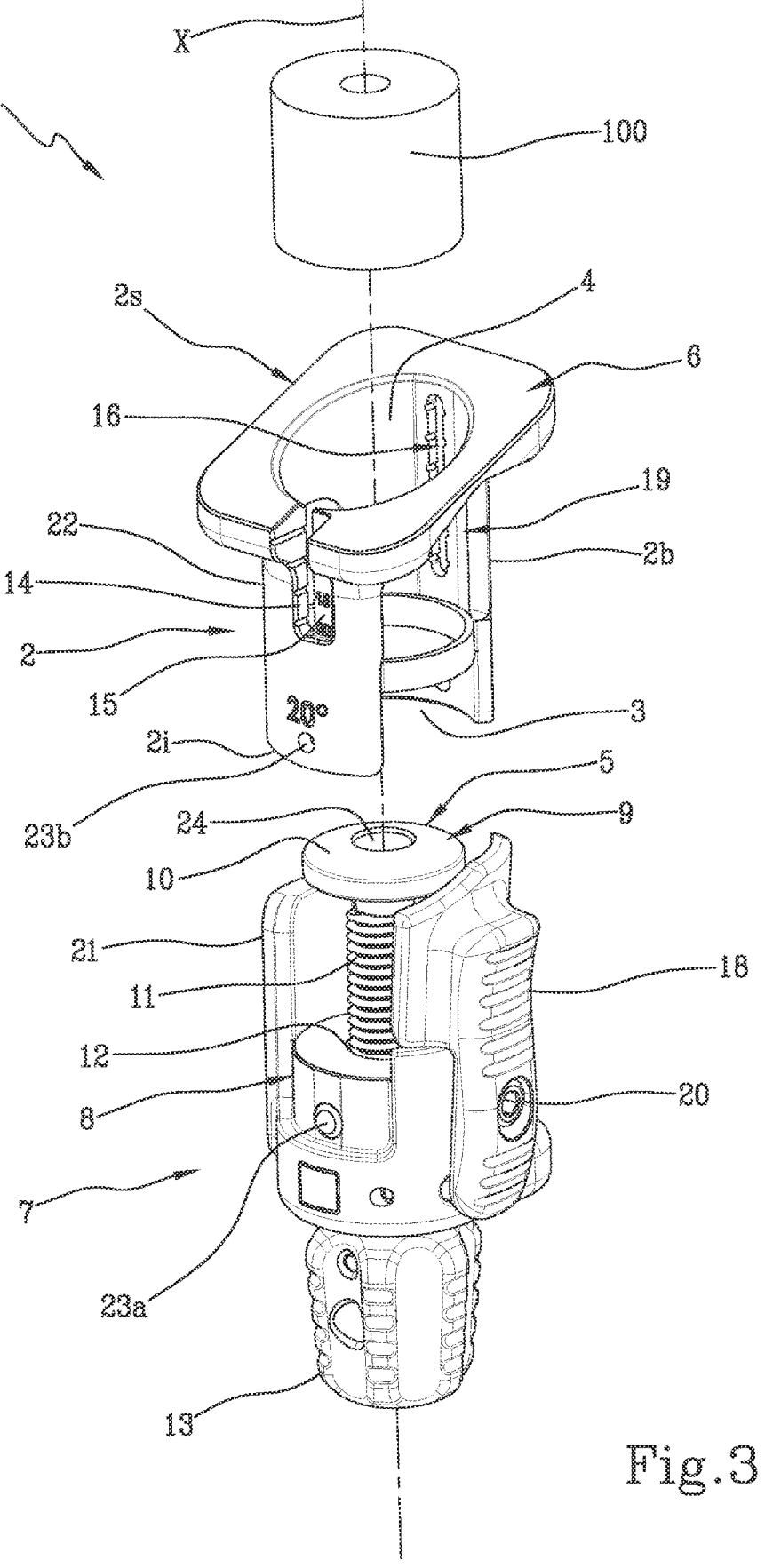
FIG. 3 illustrates an exploded perspective view of the device illustrated in FIG. 1.
Figure 4:
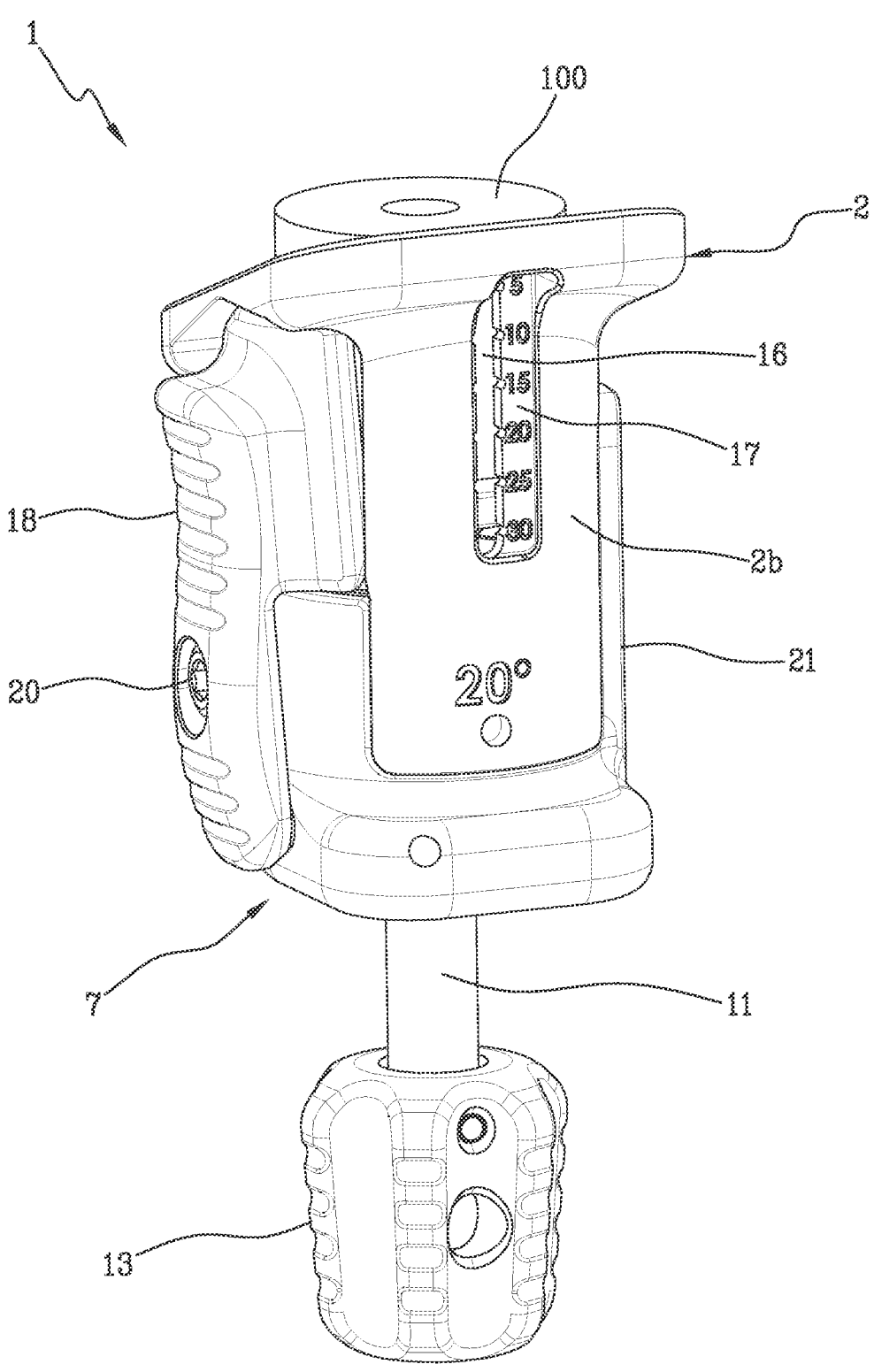
FIG. 4 illustrates a rear perspective view of the device shown in the previous figures.
Figure 6:
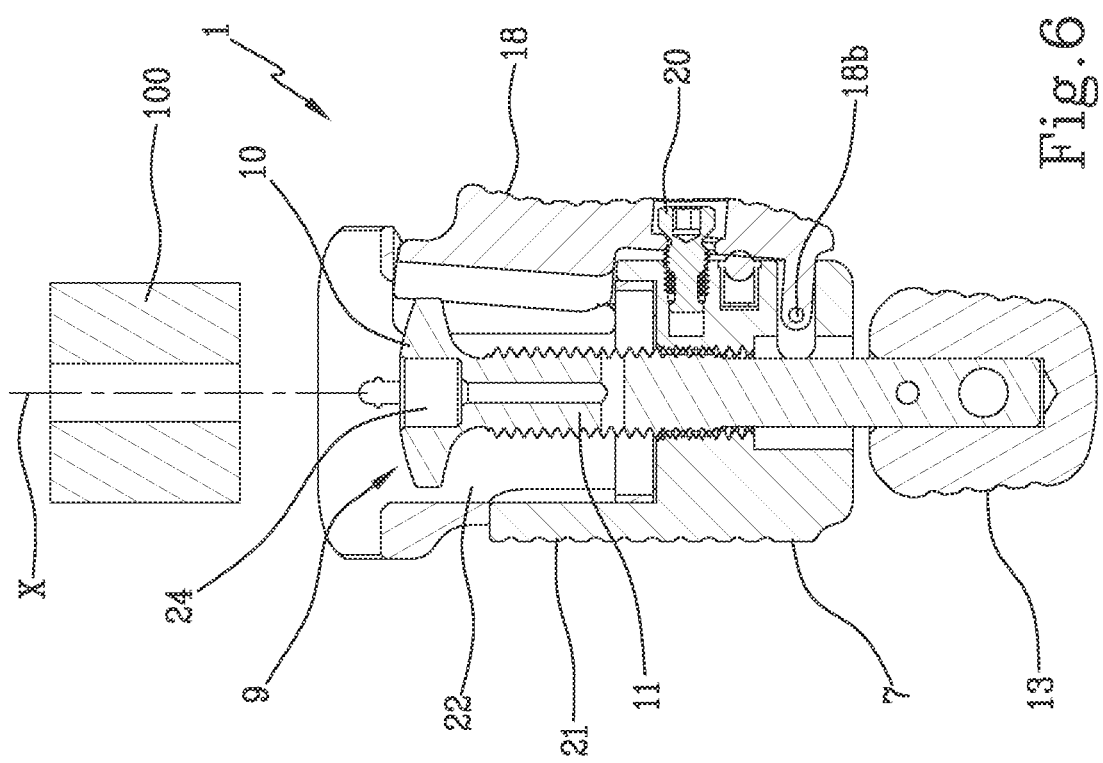
FIG. 6 illustrates a front section view of the device as shown in FIG. 5.
Figure 5:
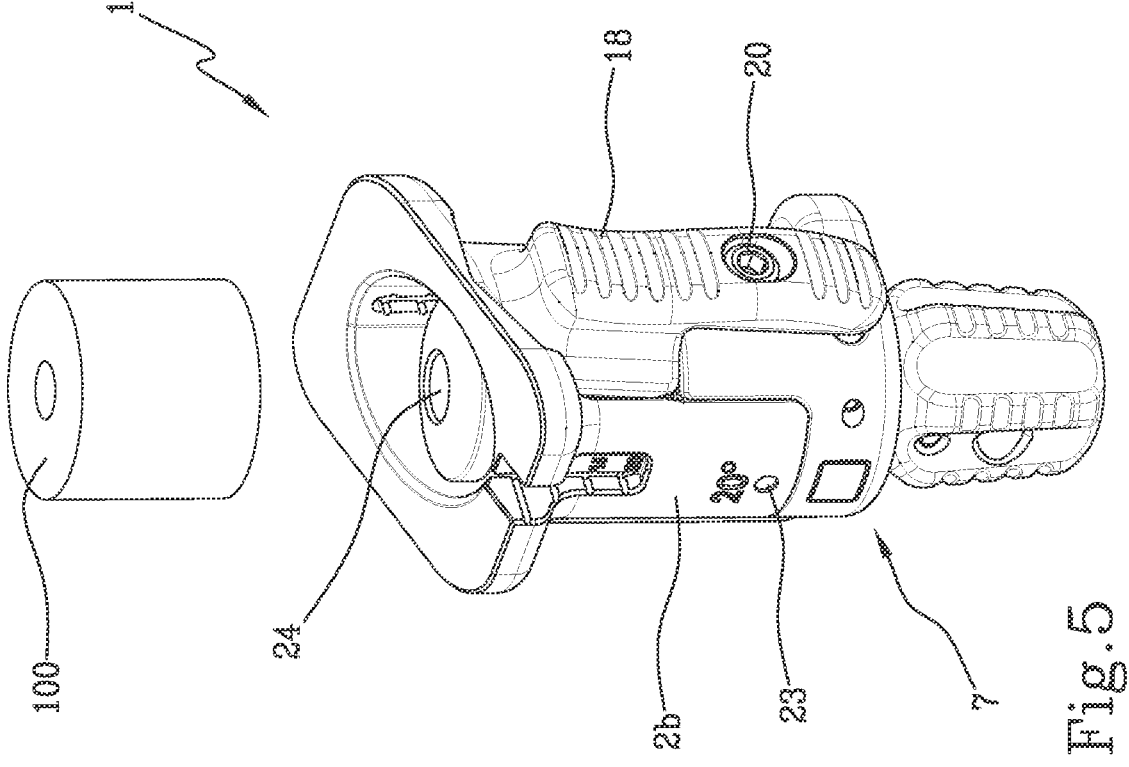
FIG. 5 illustrates a perspective view of the device shown in FIG. 1, with the bone graft separated to allow a view inside the device.
Figure 7:
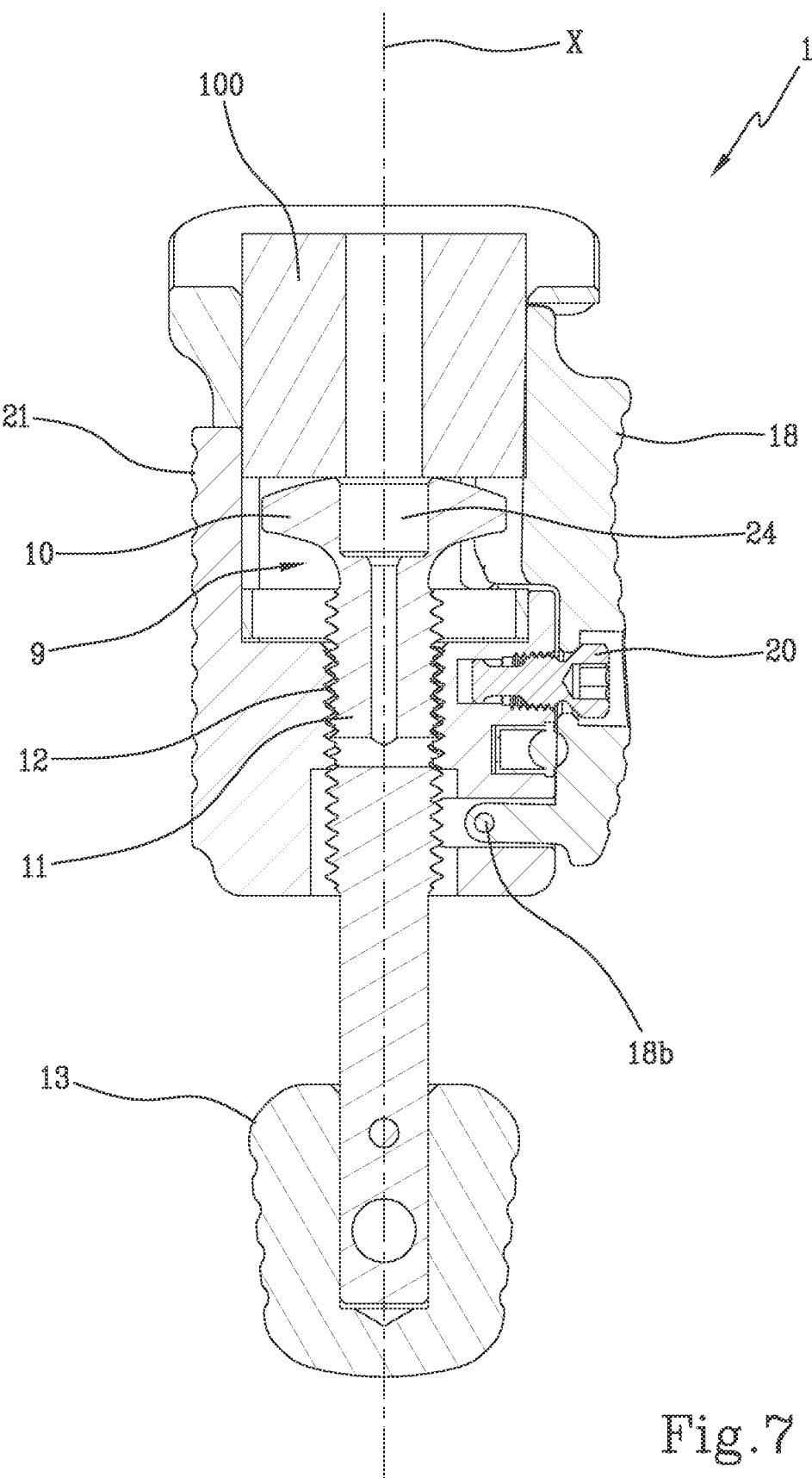
FIG. 7 shows a front section view of the device illustrated in FIG. 1.

In the non-use position, the first arm 18 is slightly spread apart from the engagement portion 8, as visible in FIG. 6, thanks to the presence of a hinge connection 18b; when the bone graft 100 is inserted inside the housing 3, the first arm 18 is clamped against the bone graft 100 either by pressure exerted by the surgeon radially from the outside towards the inside, or, by means of a locking pin 20. Said pin 20 is screwed in a clamping configuration in the first arm 18, inserting itself in the engagement portion 8: in this way, the first arm 18 holds the bone graft in a predefined locking position in order to allow the surgeon to proceed with the cutting safely and to prevent the shifting of the bone graft 100 along the longitudinal axis X. This avoids the need for the surgeon to constantly maintain pressure on the first arm 18 who can thus have the possibility to release the grip and have a free hand. In addition, by releasing the grip on the first arm, the surgeon moves his hand away from the cutting blade, preventing possible injury.

The engagement and adjustment body 7 further comprises at least a second arm 21, projecting upwards from the engagement portion 8, in order to be coupled with the main body 2. The second arm 21 is advantageously positioned in an opposite position to that of the first arm 18 with respect to the longitudinal axis X on the engagement portion 8.

The second arm 21 is mainly designed to guide the coupling between the main body 2 and the engagement and adjustment body 7.

In order to house the second arm 21 of the engagement and adjustment body 7, the main body 2 comprises at least one groove 22, on a side wall 2b thereof delimiting the housing 3 for the bone graft. As an alternative to the groove 21, the main body 2 may have a window.

To further ensure and improve the correct coupling and locking between the main body 2 and the engagement and adjustment body 7, the device 1 further comprises a centring and locking mechanism 23.

Advantageously, said centring and locking mechanism 23 comprises a ball push-button 23b, on the engagement and adjustment body 7, which can be engaged inside a hole 23c, realized on the main body 2.

Preferably, the flange head 10 comprises, on the upper surface thereof on which the bone graft rests, a central cavity 24, coaxial to the longitudinal axis X, to receive in abutment a drilling tool for the central bore of the bone graft.

The invention further provides for a kit for shaping a bone graft comprising a device according to the foregoing and a plurality of main bodies 2, each having an upper surface 6, defining a cutting plane, each having an inclination that is different from each other and predetermined with respect to the longitudinal axis X by an angle $\alpha$ ranging between 90° and 30°, preferably between 90° and 60°.

In use, the main body 2 most suitable for the dimensions and inclinations of the upper surface 6 of the bone graft to be shaped is selected and coupled with the engagement and adjustment body 7.

Once the bone graft has been extracted from the humeral head, as described above, the graft to be shaped and cut is inserted into the slit 3 of the central body 2 of the device 1, through the upper opening 4.

The height of the flange head 10 is then adjusted to the correct position, viewing the height of the flange head inside the housing 3 through the first graduated slit 14, so as to obtain a pre-established cutting height, hence a height of the bone graft.

The bone graft is held in position by clamping the first arm 18 against the side wall of the bone graft, either by simple hand pressure or by clamping the pin 20.

At this point the coupling is secured inside the device 1 and the cut can be made safely by sliding the blade on the inclined surface 6 which defines the cutting plane.

The bone graft always has an axial through hole, at least for the passage of the guide wire. Therefore, if it is necessary to ream the hole, the presence of the cavity 24 on the upper surface of the flange head 10 acts as an end stop or as a depression against which the drilling head of a suitable drilling tool abuts.

The invention achieves its intended purpose by allowing the bone graft to be shaped without being coupled to the implant, ensuring that the implant is not damaged by cutting tools during shaping.

In addition, this device allows shaping on the back table, significantly reduces surgery times and ensures a precise cutting and shaping of the bone graft.

The device subject matter of the present invention also offers the possibility of choosing different thicknesses and different angles for shaping the bone graft.

It is also possible to make the central hole in the bone graft on the back table in case of poor bone quality or allograft.

The device can therefore be used with any type of bone quality and for any type of implant.

The invention claimed is:

1. A kit for shaping and cutting a bone graft comprising a device comprising a lower support designed to support the bone graft and a plurality of main bodies, each main body extending along a longitudinal axis from a lower end to an upper end and having inside the main body a housing for insertion of the bone graft to be shaped, an upper opening defined by said upper end for the insertion of the bone graft into said housing, said upper end of the main body further comprising an upper surface defining a cutting plane, wherein the upper surface of each main body is inclined with respect to said longitudinal axis by an angle that is less than 90° and greater than or equal to 30°, the plurality of said main bodies are interchangeable, and the upper surface of each main body has an inclination that is different from other main bodies.

2. The kit according to claim 1, wherein each device comprises an engagement and adjustment body, which can be coupled to said main body, having an engagement portion, designed to receive in shape coupling the lower end of said main body, and a base portion, defining said lower support, mobile along said longitudinal axis.

3. The kit according to claim 2, wherein said base portion comprises a flange head, designed to receive in support said bone graft, connected to a threaded shank that can be screwed inside a threaded hole present in the engagement portion, and a gripping and handling element, connected to said threaded shank in a position opposite to said flange head, to rotate said base portion and cause it to shift vertically to adjust the position of the flange head inside the housing of the main body.

4. The kit according to claim 3, wherein said flange head comprises a central cavity, coaxial to said longitudinal axis, to receive in abutment a drilling tool for a central bore of the bone graft.

5. The kit according to claim 2, wherein said engagement and adjustment body comprises at least a first arm designed to guide the coupling between the main body and the engagement and adjustment body and to permanently lock the bone graft within the main body during a cutting step, by impressing a force orthogonal to the longitudinal axis on the bone graft.

6. The kit according to claim 5, wherein said engagement and adjustment body comprises at least a second arm designed to guide the coupling between the main body and the engagement and adjustment body.

7. The kit according to claim 5, wherein the main body comprises at least one window, on a side wall delimiting the housing of the bone graft, designed for the insertion of the first arm of said engagement and adjustment body.

8. The kit according to claim 6, wherein said main body comprises at least one groove, on a side wall delimiting the housing of the bone graft, designed to house the second arm of said engagement and adjustment body.

9. The kit according to claim 5, wherein it comprises a locking pin of said first arm, to lock said first arm in a clamping configuration wherein said first arm holds the bone graft in a predefined locking position to proceed with the cutting and prevent its shifting along the longitudinal axis.

10. The kit according to claim 2, wherein the kit comprises a centring and locking mechanism for correct coupling and locking between the main body and the engagement and adjustment body.

11. The kit according to claim 10, wherein said centring and locking mechanism comprises a ball push-button on the engagement and adjustment body, which can be engaged inside a hole realized on said main body.

12. The kit according to claim 1, wherein said main body defines at least one slit on a side wall delimiting the housing of the bone graft, the side wall adjacent the slit having a respective graduated scale designed to indicate a cutting height of the bone graft.

13. The kit according to claim 12, wherein said main body defines a second slit, opposite a first slit on the side wall delimiting the housing of the bone graft, the side wall adjacent the second slit having a respective graduated scale designed to indicate the cutting height of the bone graft.

14. The kit according to claim 1, wherein the upper surface is inclined with respect to said longitudinal axis by an angle that is less than 90° and greater than or equal to 60°.

\* \* \* \* \*